United States Patent
Thomas

(10) Patent No.: US 11,638,633 B2
(45) Date of Patent: May 2, 2023

(54) DISPOSABLE DENTAL VALVE HAVING A CHECK VALVE

(71) Applicant: Stoma Ventures, LLC, Chesterfield, MO (US)

(72) Inventor: Charles Thomas, Vero Beach, FL (US)

(73) Assignee: Stoma Ventures, LLC, Chesterfield, MO (US)

( * ) Notice: Subject to any disclaimer, the term of this patent is extended or adjusted under 35 U.S.C. 154(b) by 850 days.

(21) Appl. No.: 16/601,085

(22) Filed: Oct. 14, 2019

(65) Prior Publication Data

US 2021/0106413 A1    Apr. 15, 2021

(51) Int. Cl.
    *A61C 17/12*    (2006.01)
    *A61M 39/24*    (2006.01)
    *A61C 17/06*    (2006.01)

(52) U.S. Cl.
    CPC .......... *A61C 17/125* (2019.05); *A61C 17/065* (2019.05); *A61C 17/12* (2019.05); *A61C 17/13* (2019.05); *A61M 39/24* (2013.01); *A61C 17/06* (2019.05); *A61M 2039/244* (2013.01); *A61M 2205/0205* (2013.01)

(58) Field of Classification Search
    CPC ....... A61C 17/06; A61C 17/065; A61C 17/12; A61C 17/125; A61C 17/13; A61C 17/135; A61M 39/24; A61M 2039/244; A61M 2205/0205
    USPC .......................................................... 433/95
    See application file for complete search history.

(56) References Cited

U.S. PATENT DOCUMENTS

| | | | | | |
|---|---|---|---|---|---|
| 3,958,573 | A | * | 5/1976 | Wiley | A61C 17/12 604/902 |
| 4,451,257 | A | * | 5/1984 | Atchley | A61M 1/84 433/95 |
| 4,787,599 | A | * | 11/1988 | Nyboer | A61C 17/13 604/902 |
| 5,295,830 | A | * | 3/1994 | Shen | A61C 1/16 433/91 |
| 5,725,374 | A | * | 3/1998 | Young | A61C 1/18 433/95 |

(Continued)

FOREIGN PATENT DOCUMENTS

CN    103462716 A  * 12/2013
WO    WO-9947068 A1 *  9/1999    .............. A61C 1/088

OTHER PUBLICATIONS

DisposEvac HVE tips provided at www.practicon.com website, available prior to Oct. 14, 2019.

*Primary Examiner* — Matthew M Nelson
(74) *Attorney, Agent, or Firm* — David H. Chervitz

(57) ABSTRACT

A disposable dental valve device has a valve body having a tip receiving end, a hose receiving end, a lumen formed between the tip receiving end and the hose receiving end, a first partial opening formed in the valve body and a second partial opening formed in the valve body, and a movable valve sealing device adapted to being inserted into one of the partial openings, the movable valve sealing device having an opening for alignment with the lumen formed between the tip receiving end and the hose receiving end, the movable valve sealing device having a check valve positioned in the opening, and the movable valve sealing device having a top for positioning the movable valve sealing device between a closed position and an opened position.

20 Claims, 9 Drawing Sheets

(56) References Cited

U.S. PATENT DOCUMENTS

| | | | | |
|---|---|---|---|---|
| 5,882,197 | A * | 3/1999 | Davis | A61C 17/08 433/91 |
| 10,524,889 | B1 * | 1/2020 | Bordas | A61M 1/7413 |
| 11,311,361 | B1 * | 4/2022 | Tapocik | A61C 17/125 |
| 2003/0219696 | A1 * | 11/2003 | Moreland | A61C 17/08 433/91 |
| 2008/0206703 | A1 * | 8/2008 | Meeker | A61C 3/00 433/49 |
| 2009/0065067 | A1 * | 3/2009 | Bushman | A61C 17/13 137/217 |
| 2012/0003603 | A1 * | 1/2012 | Hirsch | A61C 17/022 433/32 |
| 2013/0337406 | A1 * | 12/2013 | Bordas | A61M 1/7413 433/95 |
| 2014/0170595 | A1 * | 6/2014 | Williams | A61C 17/135 433/95 |
| 2017/0273767 | A1 * | 9/2017 | Thomas | A61C 1/0061 |
| 2018/0280127 | A1 * | 10/2018 | Thomas | F16K 5/0407 |
| 2018/0280682 | A1 * | 10/2018 | Thomas | F16K 15/1848 |
| 2019/0054287 | A1 * | 2/2019 | Thomas | F16K 15/1825 |
| 2020/0397532 | A1 * | 12/2020 | Bushman | A61M 1/743 |
| 2021/0161631 | A1 * | 6/2021 | Thomas | F16K 15/16 |
| 2021/0190215 | A1 * | 6/2021 | Thomas | F16K 5/0407 |

* cited by examiner

DISPOSABLE DENTAL VALVE HAVING A CHECK VALVE

BACKGROUND

This disclosure relates to a valve for a dental instrument for removing saliva and other fluids from a mouth of a patient and more particularly to a valve for a dental instrument which incorporates a check valve for preventing backflow of saliva, debris, and other fluids back into the mouth of the patient.

During a dental procedure it is important to be able to remove saliva, blood, water, tooth fragments, metals, and other debris or fluids from the mouth of a patient. Removal of this matter allows a dentist to be able to perform a procedure in an unobstructed manner. Various systems or devices have been developed to remove liquid and solid materials from a mouth during a dental procedure. One device that is capable of removing saliva is known as a saliva ejector or a low volume ejector. A saliva ejector typically comprises a plastic flexible tube for placement in the mouth of a patient. The saliva ejector tube is connected to a valve which in turn is connected via suction tubing to a source of vacuum. In this manner, saliva is passed through the ejector tube, the valve, and the tubing to be disposed of in a sanitary manner. Once the procedure is completed, the ejector should be discarded and the valve should be sterilized by autoclaving to be used again. Although it is suggested to autoclave the valve after each use, it is known that autoclaving is hardly ever done. Another device that is capable of removing solid materials is a high volume evacuator system. A high volume evacuator system generally consists of a tube that may be inserted into a mouth of a patient with the tube connected to a valve which is connected via a tubing to a source of vacuum. Again, in this manner, debris may be removed from the mouth of the patient. After the dental procedure, the tube is disposed of and the valve should be sterilized for reuse. However, although it is suggested to sterilize the valve after use, it is known that this suggested procedure is hardly ever followed.

As can be appreciated, the saliva ejector and the high volume evacuator are used to remove liquids and debris from a mouth of a patient to prevent a patient from swallowing or aspirating liquids and debris produced during a dental procedure. Typically, when using these evacuator devices there is no backflow back into the mouth of a patient. However, there are times when backflow or a reverse flow may take place and previously removed liquids and debris may flow back into the mouth of the patient. It is also possible that if the systems are not properly maintained that fluids and debris from a previous patient may flow back into the mouth of a subsequent patient. These situations may be dangerous, are undesirable, and should be avoided.

In order to prevent backflow, there are various devices that are separate from the saliva ejector. These devices are inserted between the flexible tube and the dental valve or between the dental valve and suction tubing. These devices tend to be complex and expensive. Further, these devices have to be separately purchased, inventoried, and used apart from the flexible tube and the dental valve.

Therefore, it would be desirable to have a valve for a dental instrument that incorporates a check valve for preventing a backflow condition. It would also be desirable to have a disposable dental valve having a check valve that is easy to install on or remove from suction tubing for a source of vacuum. Further, it would be advantageous to have a disposable dental valve having a check valve that is disposable.

BRIEF SUMMARY

In one form of the present disclosure, a disposable dental valve device comprises a valve body having a tip receiving end, a hose receiving end, a lumen formed between the tip receiving end and the hose receiving end, a first partial opening formed in the valve body and a second partial opening formed in the valve body, and a movable valve sealing device adapted to being inserted into one of the partial openings, the movable valve sealing device having an opening for alignment with the lumen formed between the tip receiving end and the hose receiving end, the movable valve sealing device having a check valve positioned in the opening, and the movable valve sealing device having a top for positioning the movable valve sealing device between a closed position and an opened position.

In another form of the present disclosure, a disposable dental valve device comprises a valve body having a tip receiving end, a hose receiving end, a lumen formed between the tip receiving end and the hose receiving end, an upper extension portion formed in the valve body having an upper opening formed in the upper extension portion and a lower extension portion formed in the valve body, and a movable valve sealing device adapted to being inserted into the upper opening, the movable valve sealing device having an opening for alignment with the lumen formed between the tip receiving end and the hose receiving end, the movable valve sealing device having a check valve positioned in the opening, and the movable valve sealing device having a top for moving the movable valve sealing device into an opened position and a closed position.

In yet another form of the present disclosure, a disposable dental valve device kit comprises a valve body having a tip receiving end, a hose receiving end, a lumen formed between the tip receiving end and the hose receiving end, a first partial opening formed in the valve body and a second partial opening formed in the valve body, a movable valve sealing device adapted to being inserted into one of the partial openings, the movable valve sealing device having an opening for alignment with the lumen formed between the tip receiving end and the hose receiving end, the movable valve sealing device having a check valve positioned in the opening, and the movable valve sealing device having a top for positioning the movable valve sealing device between a closed position and an opened position, and a cap device for insertion into a hose connected to a source of vacuum.

The present disclosure provides a disposable dental valve device having a check valve for use with a dental instrument that is suitable for one time use and may be discarded after a single use.

The present disclosure provides a disposable dental valve device having a check valve that is easy to install on suction tubing connected to a source of vacuum and have a tip installed on another end of the disposable dental valve device.

The present disclosure provides a disposable dental valve device having a check valve that is small, lightweight, easy to handle, easy to install, and easy to operate.

The present disclosure also provides a disposable dental valve device having a check valve which is of simple construction and design and which can be easily employed with highly reliable results.

The present disclosure is related to a disposable dental valve device having a check valve that does not require sterilization and prevents against any backflow and cross-contamination.

The present disclosure provides a disposable dental valve device having a check valve that may have an antimicrobial agent or chemical incorporated into the device to prevent any bacterial growth on the device. The antimicrobial agent or chemical may also be a coating applied to the disposable dental valve device having a check valve.

The present disclosure is related to a disposable dental valve device having a check valve that may be constructed of plastic that is recyclable or biodegradable to reduce the cost of the device and to allow the device to be disposable and discarded after a single use.

The present disclosure provides a disposable dental valve device having a check valve that further includes a cap device that may be used to cap off a suction tubing connected to a source of vacuum when the disposable dental valve device having a check valve is removed from the suction tubing connected to the source of vacuum to reduce or eliminate any sound or noise associated with the source of vacuum.

The present disclosure is related to a disposable dental valve device having a check valve that has a valve sealing body that is easy to manipulate during a dental operation to open or close the valve and also incorporates a check valve to automatically prevent backflow of saliva, liquid, or other material.

The present disclosure is also related to a disposable dental valve device having a check valve that does not require a twisting or rotating motion to open or close the valve.

These and other advantages of the present disclosure will become apparent after considering the following detailed specification in conjunction with the accompanying drawings, wherein:

DETAILED DESCRIPTION OF A PREFERRED EMBODIMENT

Figure 1:
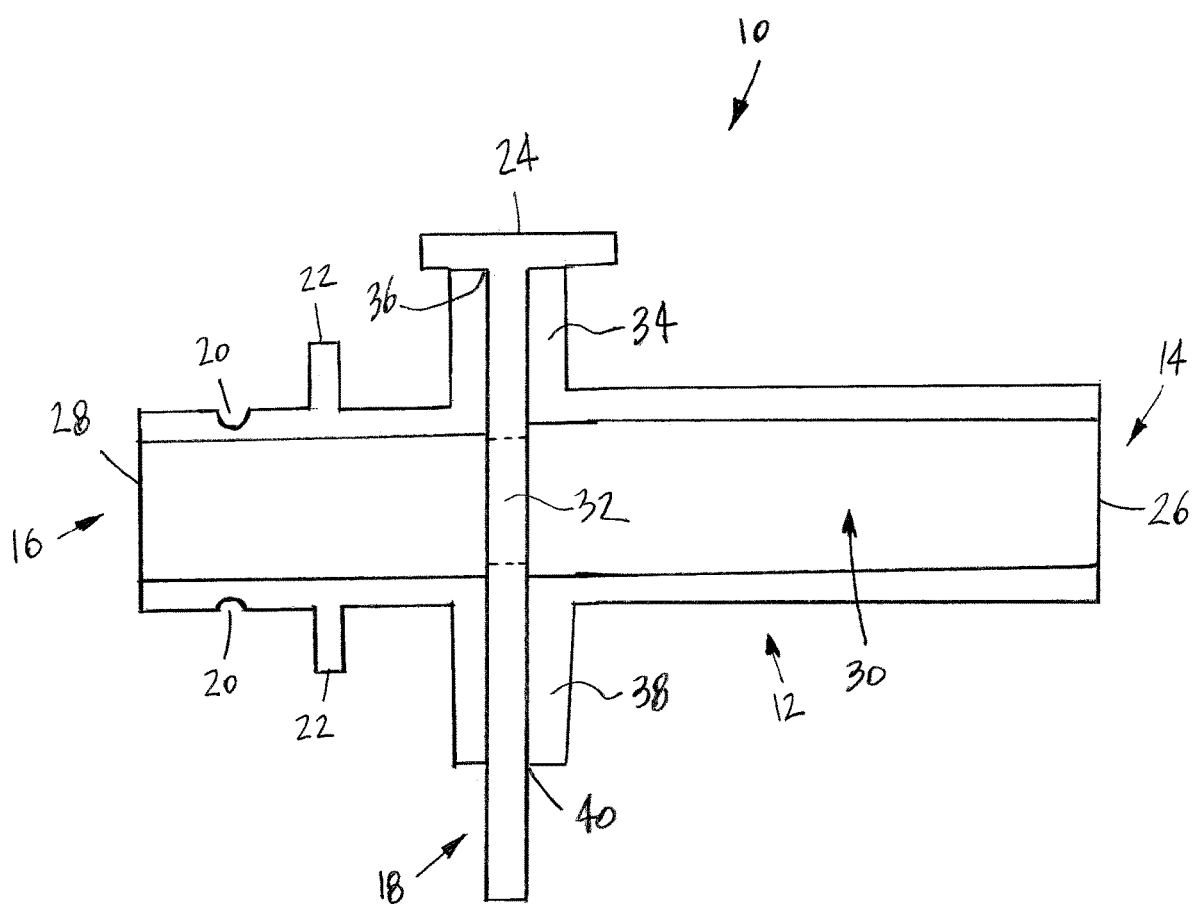
FIG. 1 is a cross-sectional view of a disposable dental valve device constructed according to the present disclosure.

Referring now to the drawings, wherein like numbers refer to like items, number 10 identifies a disposable dental valve device for use with a dental system (not shown) constructed according to the present disclosure. With reference now to FIG. 1, the valve device 10 comprises a valve body 12 having a tip receiving end 14, a suction tubing or hose receiving end 16, and a movable valve sealing body 18. The tip receiving end 14 is adapted to receive an evacuator tip device or straw (not shown) such as a high volume evacuator or a low volume evacuator (saliva ejector). The hose receiving end 16 is adapted to receive a vacuum line or a hose or a tailpiece (not shown) which is connected to a suction system (also not shown) which is used to dispose of any saliva, liquid, or debris removed from a mouth of a patient. The hose receiving end 16 also has a circumferential channel 20 that is adapted to accept an O-ring (not shown). The O-ring is used to further secure a hose or a tailpiece (not shown) to the hose receiving end 16. It is also possible that the hose receiving end 16 may incorporate a structure to secure a hose to the end 16 without the use of the channel 20 or the requirement for an O-ring. For example, the end 16 may be barbed so that the barbs may hold a hose thereon. The device 10 is constructed of material that allows the device 10 to be disposable and suitable for one time use. The hose receiving end 16 also has a circular stop 22 which is used to position a hose or a tailpiece at a particular point on the valve body 12. The movable valve sealing body 18 has a top or a handle 24 for allowing an individual to grasp the movable valve sealing body 18 for manual operation of the movable valve sealing body 18. Manual operation of the top 24 will open the device 10, close the device 10, or partially open the device 10, as will be discussed more fully herein. As can be appreciated, a suction system provides suction through an evacuator tip device, the device 10, and a hose so that any debris, liquid, or saliva that is introduced into an evacuator tip device is removed through an evacuator tip device, the valve 10, and a hose when the movable valve sealing body 18 of the device 10 is in an open state or a partially open state. The valve body 12 also has an opening 26 at the tip receiving end 14 and an opening 28 at the hose receiving end 16. A passage or lumen 30 is formed in the valve body 12. The lumen 30 spans between the tip receiving end 14 to the hose receiving end 16. Although not shown, it is contemplated that the tip receiving end 14 may be constructed having an interior annular ring for receiving an O-ring to retain a tip therein. It is also possible that the tip receiving end 14 may have other structure that will allow a frictional engagement of a tip and the tip receiving end 14. The movable valve sealing device 18 also has an opening 32 formed therein for allowing the passage of any saliva, liquid, or debris to pass there through when the movable valve sealing device 18 is in an opened position, as is depicted in FIG. 1. The valve body 12 also has an upper extension portion 34 formed therein with the portion having an upper opening 36. A lower extension portion 38 is formed in the valve body 12 having a lower opening 40. The movable valve sealing body 18 is capable of sliding or moving through the openings 36 and 40. In particular, the movable valve sealing body 18 may be positioned to a closed position by grasping the top 24 and moving the top 24 upwardly so that the opening 32 is not within the lumen 30 and thereby blocking any suction or air flow. In essence, the opening 32 is now positioned in the upper extension portion 34 when the valve device 10 is in the closed position.

Figure 2:
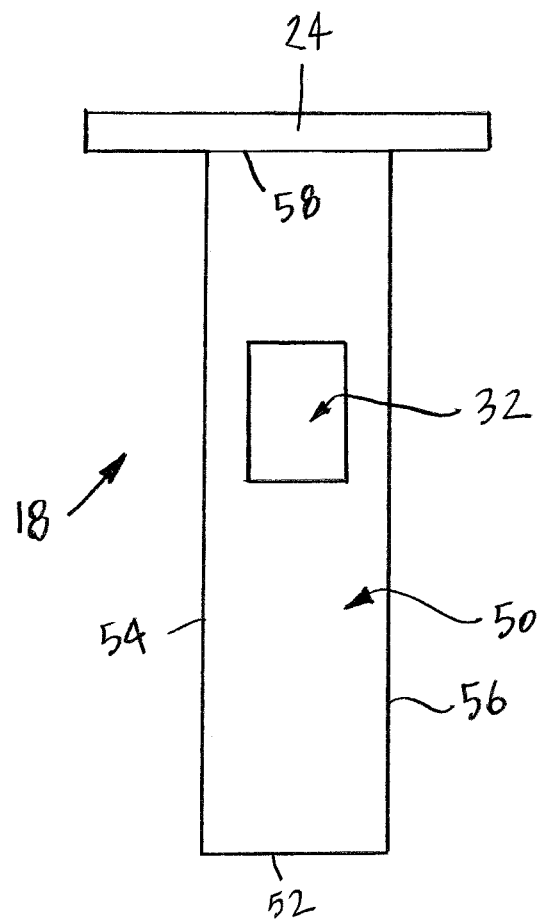
FIG. 2 is a front view of a movable valve sealing body removed from the disposable dental valve device constructed according to the present disclosure.

With reference now to FIG. 2, the movable valve sealing device 18 is illustrated being removed from the valve body 12. The movable valve sealing device 18 has a generally rectangular panel 50 having a bottom side 52, a left side 54, a right side 56, and a top side 58 at which the handle 24 is positioned. The opening 32 is shown as being a generally rectangular opening for allowing any liquid, saliva, or debris to pass through when the valve device 10 is in an opened position. Although the opening 32 is depicted as being generally rectangular in shape it is possible that the opening 32 may be any suitable size and shape such as round, oval, square, or triangular. As can be appreciated, the movable valve sealing device 18 is inserted into the valve body 12 by inserting the bottom side 52 into the upper opening 36 of the upper extension portion 34 (FIG. 1).

Figure 3:
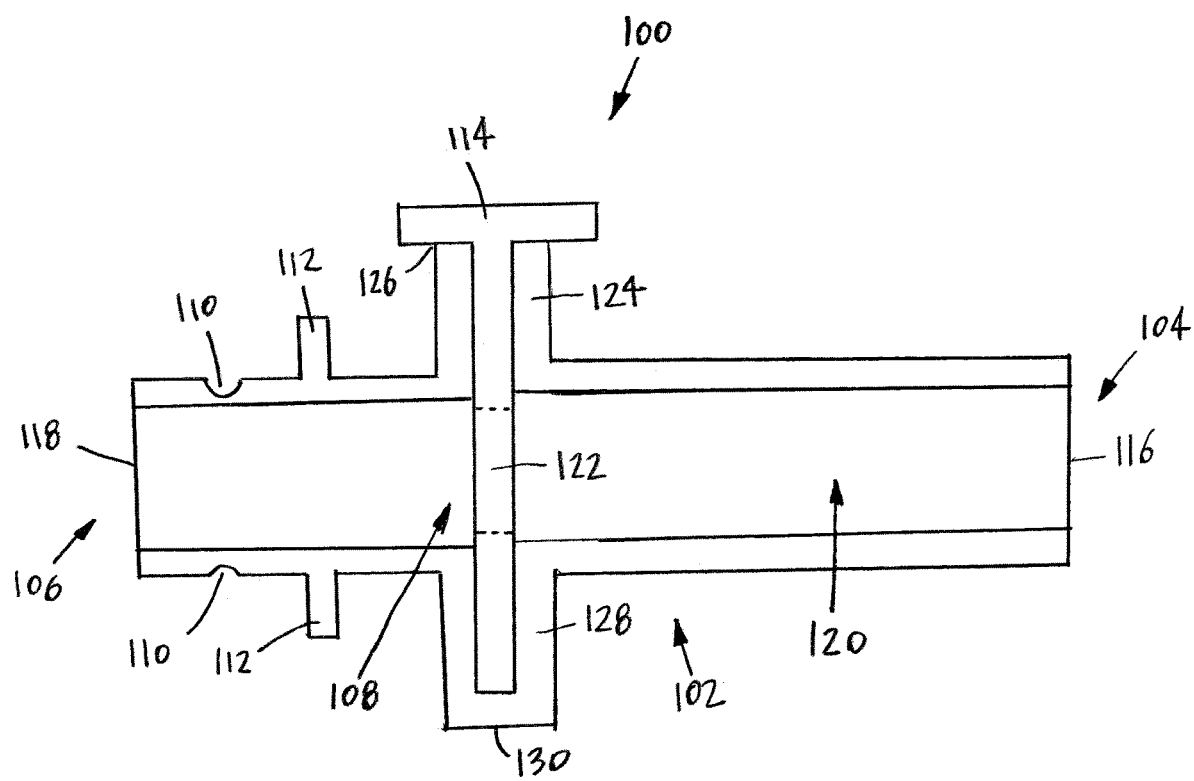
FIG. 3 is a cross-sectional view of another embodiment of a disposable dental valve device constructed according to the present disclosure.

FIG. 3 shows a cross-sectional view of another embodiment of a disposable dental valve device 100 constructed according to the present disclosure. The valve device 100 comprises a valve body 102 having a tip receiving end 104, a suction tubing or hose receiving end 106, and a movable valve sealing body 108. The tip receiving end 104 is adapted to receive an evacuator tip device or straw (not shown) such as a high volume evacuator or a low volume evacuator (saliva ejector). The hose receiving end 106 is adapted to receive a vacuum line or a hose or a tailpiece (not shown) which is connected to a suction system (also not shown) which is used to dispose of any saliva, liquid, or debris removed from a mouth of a patient. The hose receiving end 106 also has a circumferential channel 110 that is adapted to accept an O-ring (not shown). The O-ring is used to further secure a hose or a tailpiece to the hose receiving end 106. It is also possible that the hose receiving end 106 may incorporate a structure to secure a hose to the end 106 without the use of the channel 110 or the requirement for an O-ring. For example, the end 106 may be barbed so that the barbs may hold a hose thereon. The device 100 is constructed of material that allows the device 100 to be disposable and suitable for one time use. The hose receiving end 106 also has a circular stop 112 which is used to position a hose or a tailpiece at a particular point on the valve body 102. The movable valve sealing body 108 has a top or a handle 114 for allowing an individual to grasp the movable valve sealing body 108 for manual operation of the movable valve sealing body 108. Manual operation of the top 114 will open the device 100, close the device 100, or partially open the device 100. As can be appreciated, a suction system provides suction through an evacuator tip device, the device 100, and a hose so that any debris, liquid, or saliva that is introduced into an evacuator tip device is removed through an evacuator tip device, the valve 100, and a hose when the movable valve sealing body 108 of the device 100 is in an open state or a partially open state. The valve body 102 also has an opening 116 at the tip receiving end 104 and an opening 118 at the hose receiving end 106. A passage or lumen 120 is formed in the valve body 102. The lumen 120 spans between the tip receiving end 104 to the hose receiving end 106. Although not shown, it is contemplated that the tip receiving end 104 may be constructed having an interior annular ring for receiving an O-ring to retain a tip therein. It is also possible that the tip receiving end 104 may have other structure that will allow a frictional engagement of a tip and the tip receiving end 104. The movable valve sealing device 108 also has an opening 122 formed therein for allowing the passage of any saliva, liquid, or debris to pass there through when the movable valve sealing device 108 is in an opened position, as is depicted in FIG. 3. The valve body 102 also has an upper extension portion 124 formed therein with the portion 124 having an upper opening 126. A lower extension portion 128 is formed in the valve body 102 having a lower portion 130. The movable valve sealing body 108 is capable of sliding or moving through the opening 126. In particular, the movable valve sealing body 108 may be positioned to a closed position by grasping the top 114 and moving the top 114 upwardly so that the opening 122 is not within the lumen 120 and thereby blocking any suction or air flow. In essence, the opening 122 is now positioned in the upper extension portion 124 when the valve device 100 is in the closed position. A difference between the valve device 10 and the valve device 100 is that the valve device 100 has the lower portion 130 that further seals the valve device 100.

Figure 4:
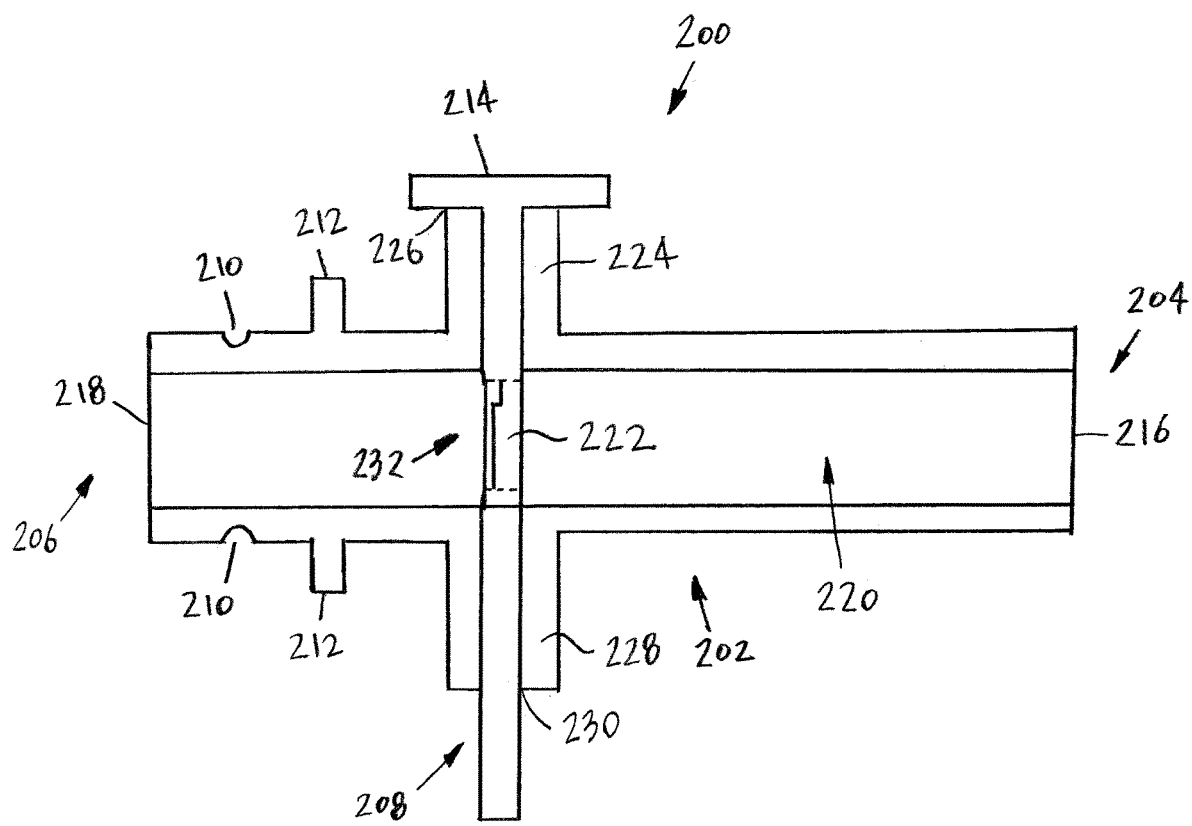
FIG. 4 is a cross-sectional view of another embodiment of a disposable dental valve device constructed according to the present disclosure.

With reference now to FIG. 4, another embodiment of a disposable dental valve device 200 constructed according to the present disclosure is illustrated. The valve device 200 comprises a valve body 202 having a tip receiving end 204, a suction tubing or hose receiving end 206, and a movable valve sealing body 208. The tip receiving end 204 is adapted to receive an evacuator tip device or straw (not shown) such as a high volume evacuator or a low volume evacuator (saliva ejector). The hose receiving end 206 is adapted to receive a vacuum line or a hose or a tailpiece (not shown) which is connected to a suction system (also not shown) which is used to dispose of any saliva, liquid, or debris removed from a mouth of a patient. The hose receiving end 206 also has a circumferential channel 210 that is adapted to accept an O-ring (not shown). The O-ring is used to further secure a hose or a tailpiece (not shown) to the hose receiving end 206. It is also possible that the hose receiving end 206 may incorporate a structure to secure a hose to the end 206 without the use of the channel 210 or the requirement for an O-ring. For example, the end 206 may be barbed so that the barbs may hold a hose thereon. The device 200 is constructed of material that allows the device 200 to be disposable and suitable for one time use. The hose receiving end 206 also has a circular stop 212 which is used to position a hose or a tailpiece at a particular point on the valve body 202. The movable valve sealing body 208 has a top or a handle 214 for allowing an individual to grasp the movable valve sealing body 208 for manual operation of the movable valve sealing body 208. Manual operation of the top 214 will open the device 200, close the device 200, or partially open the device 200. As can be appreciated, a suction system provides suction through an evacuator tip device, the device 200, and a hose so that any debris, liquid, or saliva that is introduced into an evacuator tip device is removed through an evacuator tip device, the valve 200, and a hose when the movable valve sealing body 208 of the device 200 is in an open state or a partially open state. The valve body 202 also has an opening 216 at the tip receiving end 204 and an opening 218 at the hose receiving end 206. A passage or lumen 220 is formed in the valve body 202. The lumen 220 spans between the tip receiving end 204 to the hose receiving end 206. Although not shown, it is contemplated that the tip receiving end 204 may be constructed having an interior annular ring for receiving an O-ring to retain a tip therein. It is also possible that the tip receiving end 204 may have other structure that will allow a frictional engagement of a tip and the tip receiving end 204. The movable valve sealing device 208 also has an opening 222 formed therein for allowing the passage of any saliva, liquid, or debris to pass there through when the movable valve sealing device 208 is in an opened position, as is depicted in FIG. 4. The valve body 202 also has an upper extension portion 224 formed therein with the portion having an upper opening 226. A lower extension portion 228 is formed in the valve body 202 having a lower opening 230. The movable valve sealing body 208 is capable of sliding or moving through the openings 226 and 230. In particular, the movable valve sealing body 208 may be positioned to a closed position by grasping the top 214 and moving the top 214 upwardly so that the opening 222 is not within the lumen 220 and thereby blocking any suction or air flow. In essence, the opening 222 is now positioned in the upper extension portion 224 when the valve device 200 is in the closed position.

The opening 222 also has a check valve 232 that is inset into the movable valve sealing device 208. The check valve 232 is used to prevent backflow of the device 200. The check valve 232 is positioned in the opening 222 to selectively open or close the opening 222. The check valve 232 is provided for allowing liquid, saliva, or debris to pass from the tip receiving end 204, the opening 222, the check valve 232, and out the hose receiving end 206 when the check valve 232 is opened. However, the check valve 232 also prevents any liquid, saliva, or debris from passing or traveling from the hose receiving end 206 and through the check valve 232 when the check valve 232 is closed. The check valve 232 will close when a reduced pressure occurs from an interaction of a mouth of a patient on an evacuator tip device. For example, a patient may be requested to close the mouth of the patient around the evacuator tip device. When this occurs, a reduced pressure results in which a backflow may occur. The check valve 232 is sensitive to this pressure differential and will close to prevent backflow. The check valve 232 is shown in the closed position in FIG. 4. As can be appreciated, when the opening 222 is aligned with the lumen 220, the device 200 is in an opened position and the source of vacuum will draw any fluid, saliva, or debris from the tip receiving end 204 through the lumen 220, the opening 222, the check valve 232, and out through the hose receiving end 206. The check valve 232 will be in an opened position or configuration at this particular time. In this manner, fluid, saliva, and debris may be removed from a mouth of a patient during a dental procedure or operation.

Figure 5:
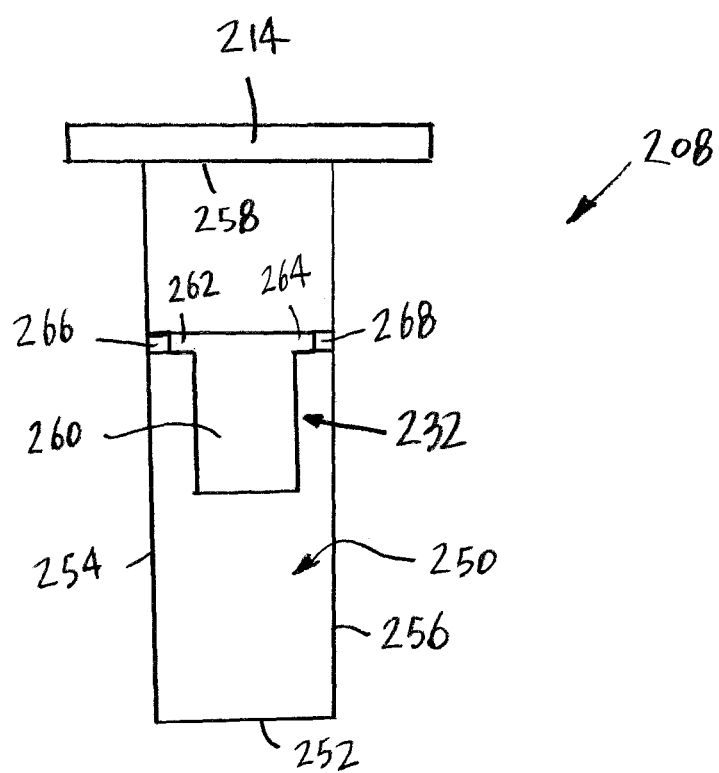
FIG. 5 is a back view of the movable valve sealing body shown in FIG. 4 being removed from the disposable dental valve device constructed according to the present disclosure.

FIG. 5 shows a back side of the movable valve sealing device 208 being removed from the valve body 202. The movable valve sealing device 208 has a generally rectangular panel 250 having a bottom side 252, a left side 254, a right side 256, and a top side 258 at which the handle 214 is positioned. The opening 222, not visible in this particular view, is covered by the check valve 232. The check valve 232 comprises a flap portion 260 having a pair of upper arms 262 and 264 which extend into and are captured by a pair of corresponding pockets 266 and 268. It is also possible that the panel 250 may have a recess, groove, or rabbet formed therein to receive or seat the flap portion 260 therein so that the flap portion 260 is flush with the panel 250. This allows for the movable valve sealing device 208 to be moved without being restricted within the valve body 202. The connection of the flap portion 260 to the panel 250 by the use of the arms 262 and 264 and the pockets 266 and 268 allows the check valve 232 to easily open or close. The flap portion 260 may also include a hinge device that allows the flap portion 260 to move or swing relative to the movable valve sealing device 208. Although the panel 250 is depicted as being generally rectangular in shape it is possible that the panel 250 may be any suitable shape such as round, oval, square, or triangular. The opening 222 may also be any suitable shape. Although the arms 262 and 264 and the pockets 266 and 268 are shown, it is possible that other retention or engagement type constructions are contemplated, such as using an adhesive or forming the panel 250 and the flap portion 260 as a unitary piece or construction.

Figure 6:
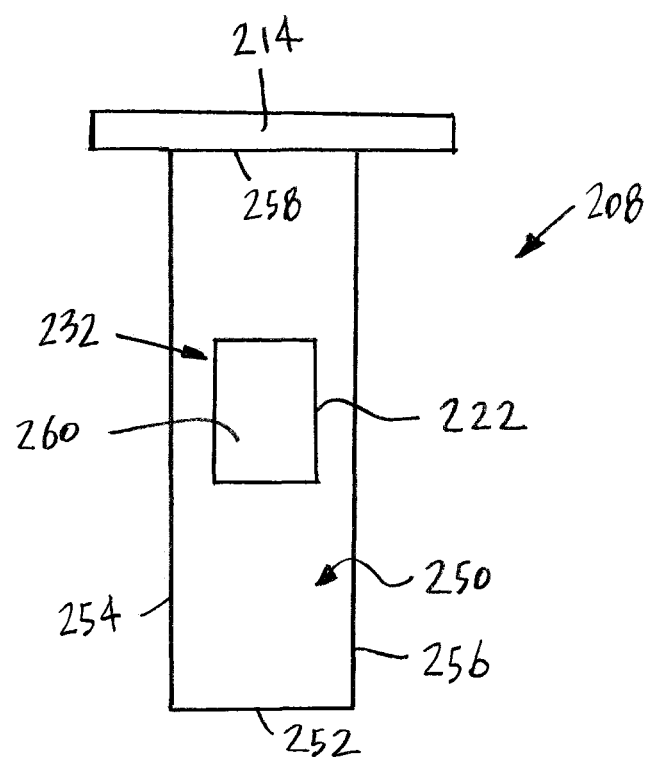
FIG. 6 is a front view of the movable valve sealing body shown in FIG. 4 being removed the disposable dental valve device constructed according to the present disclosure.

Referring now to FIG. 6, a front side of the movable valve sealing device 208 being removed from the valve body 202 is shown. The movable valve sealing device 208 has the generally rectangular panel 250 having the bottom side 252, the left side 254, the right side 256, the top side 258, and the handle 214. The opening 222, which is visible in this particular view, is shown as being a generally rectangular opening for allowing any liquid, saliva, or debris to pass through when the valve device 200 and the check valve 232 are in an opened position. The check valve 232 comprises the flap portion 260 which covers the opening 222 when the check valve 232 is in the closed position, as is shown.

Figure 7:
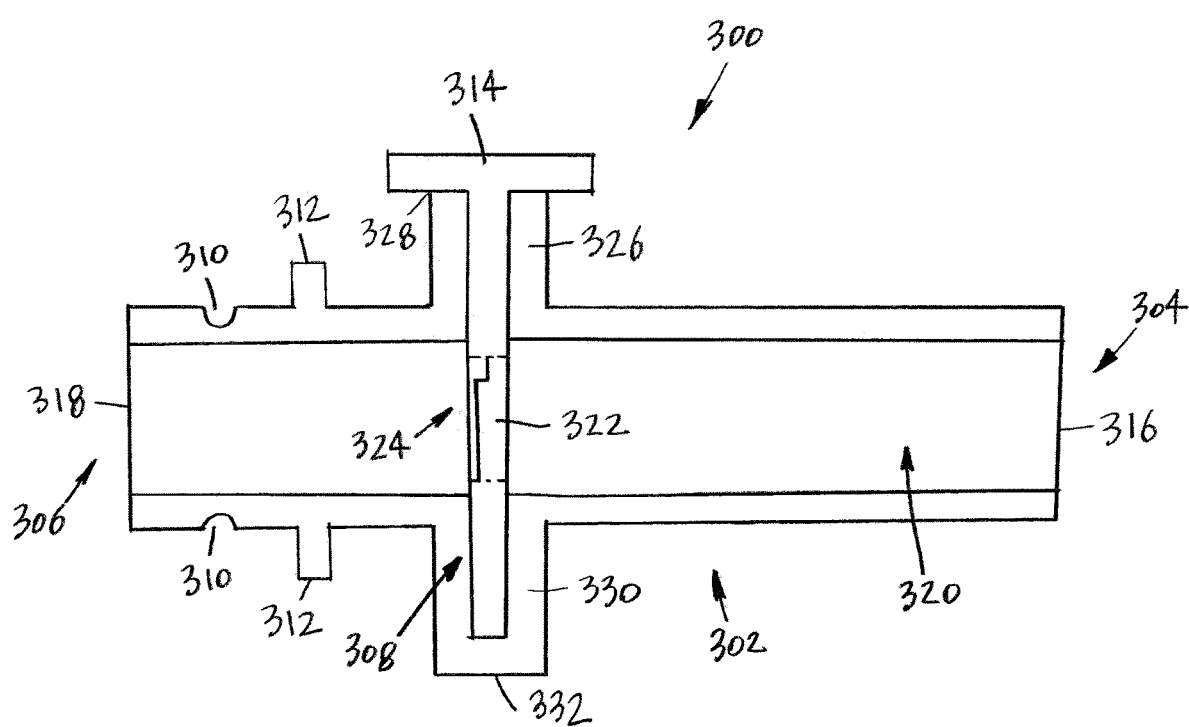
FIG. 7 is a cross-sectional view of another embodiment of a disposable dental valve device constructed according to the present disclosure.

FIG. 7 illustrates a cross-sectional view of another embodiment of a disposable dental valve device 300 constructed according to the present disclosure. The valve device 300 comprises a valve body 302 having a tip receiving end 304, a suction tubing or hose receiving end 306, and a movable valve sealing body 308. The tip receiving end 304 is adapted to receive an evacuator tip device or straw (not shown) such as a high volume evacuator or a low volume evacuator (saliva ejector). The hose receiving end 306 is adapted to receive a vacuum line or a hose or a tailpiece (not shown) which is connected to a suction system (also not shown) which is used to dispose of any saliva, liquid, or debris removed from a mouth of a patient. The hose receiving end 306 also has a circumferential channel 310 that is adapted to accept an O-ring (not shown). The O-ring is used to further secure a hose or a tailpiece to the hose receiving end 306. It is also possible that the hose receiving end 306 may incorporate a structure to secure a hose to the end 306 without the use of the channel 310 or the requirement for an O-ring. For example, the end 306 may be barbed so that the barbs may hold a hose thereon. The device 300 is constructed of material that allows the device 300 to be disposable and suitable for one time use. The hose receiving end 306 also has a circular stop 312 which is used to position a hose or a tailpiece at a particular point on the valve body 302. The movable valve sealing body 308 has a top or a handle 314 for allowing an individual to grasp the movable valve sealing body 308 for manual operation of the movable valve sealing body 308. Manual operation of the top 314 will open the device 300, close the device 300, or partially open the device 300. As can be appreciated, a suction system provides suction through an evacuator tip device, the device 300, and a hose so that any debris, liquid, or saliva that is introduced into an evacuator tip device is removed through an evacuator tip device, the valve 300, and a hose when the movable valve sealing body 308 of the device 300 is in an open state or a partially open state. The valve body 302 also has an opening 316 at the tip receiving end 304 and an opening 318 at the hose receiving end 306. A passage or lumen 320 is formed in the valve body 302. The lumen 320 spans between the tip receiving end 304 to the hose receiving end 306. Although not shown, it is contemplated that the tip receiving end 304 may be constructed having an interior annular ring for receiving an O-ring to retain a tip therein. It is also possible that the tip receiving end 304 may have other structure that will allow a frictional engagement of a tip and the tip receiving end 304. The movable valve sealing device 308 also has an opening 322 formed therein and a check valve 324 for allowing the passage of any saliva, liquid, or debris to pass there through when the movable valve sealing device 308 is in an opened position. The valve body 302 also has an upper extension portion 326 formed therein with the portion 326 having an upper opening 328. A lower extension portion 330 is formed in the valve body 302 having a lower portion 332. The movable valve sealing body 308 is capable of sliding or moving through the upper opening 328. In particular, the movable valve sealing body 308 may be positioned to a closed position by grasping the top 314 and moving the top 314 upwardly so that the opening 322 is not within the lumen 320 and thereby blocking any suction or air flow. In essence, the opening 322 is now positioned in the upper extension portion 326 when the valve device 300 is in the closed position. The check valve 324 is similar in construction and operation as the check valve 232.

Figure 8:
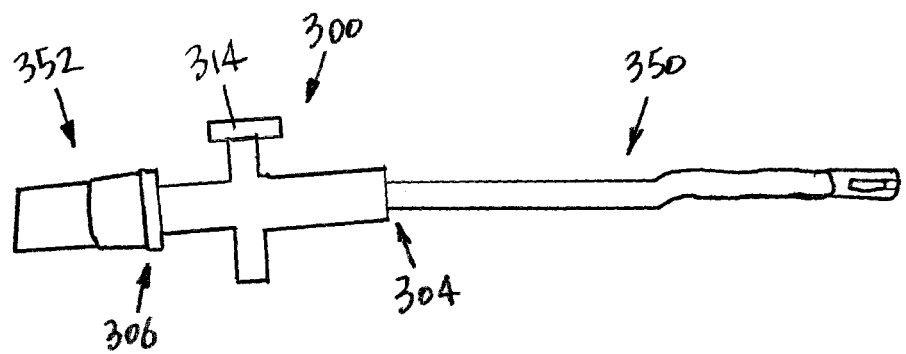
FIG. 8 is a perspective view of a disposable dental valve device being connected to a hose and a tip device.

Referring now in particular to FIG. 8, the valve device 300 is shown being connected to an evacuator tip device 350 at the tip receiving end 304 and to a tailpiece 352 at the hose receiving end 306. The valve device 300 is shown in the opened position and any saliva, liquid, or debris may pass through the tip device 350, the valve device 300, and the tailpiece 352. In operation of the valve device 300, the tailpiece 352 is connected to a hose (not shown) which is connected to a suction system (also not shown). The evacuator tip device 350 is placed in a mouth of a dental patient. The top 314 is manually operated to open the device 300. Once in the opened position, air is allowed to flow through the tip device 350, the tip receiving end 304, the lumen 320, the opening 322, the check valve 324, the hose receiving end 306 and into a suction system. In the event that reduced pressure occurs from an interaction of a mouth of a patient on the evacuator tip device 350, the check valve 324 will close and no backflow will be allowed from the suction system or the valve device 300. When suction is not needed during a dental procedure, the top 314 is moved to the closed position. Once the device 300 is disconnected from the hose, the device 300 may be disposed of by any suitable manner. A new device 300 is then connected to the tailpiece 352 and a new tip device 350 is connected to the new device 300. With the new valve device 300 installed, another dental procedure may be initiated.

Figure 9:
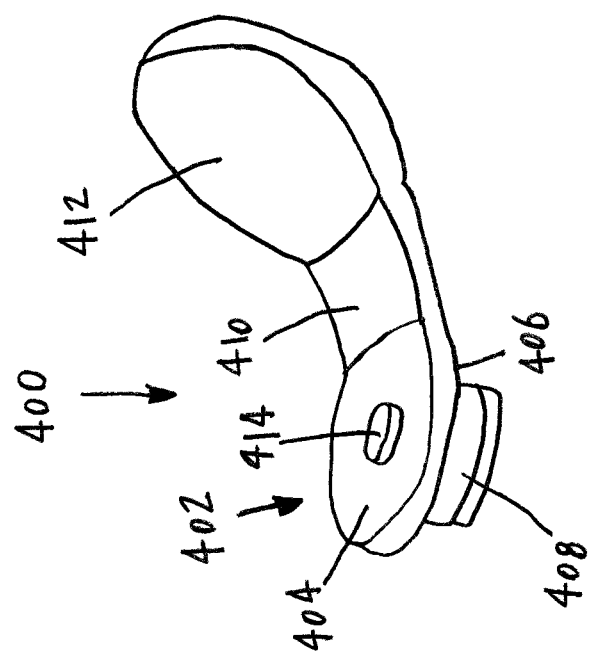
FIG. 9 is a perspective view of cap device constructed according to the present disclosure

Referring now in particular to FIG. 9, a cap device 400 is depicted which is used to be placed over the opening of a suction tubing or hose or a tailpiece (all of which are not shown) when any of the devices 10, 100, 200, or 300 are removed from the hose or tailpiece to remove or dispose the devices 10, 100, 200, and 300. In this manner, the opening of the hose will be physically blocked to shut off any air from rushing into the hose to silence any noise produced by the suction system or a source of vacuum. The cap device 400 is sized and shaped to fit over the opening of the hose. The cap device 400 may be constructed of any suitable material such as rubber or plastic. The valve devices 10, 100, 200, and 300 may include the cap device 400 so that when the valve devices 10, 100, 200, and 300 are removed from the hose for disposal after use the cap device 400 may be placed over the opening of the hose. The cap device 400 comprises a body portion 402 having a top side 404 and a bottom side 406 with the bottom side 406 having a plug portion 408. A central portion 410 is connected between the body portion 402 and a pull 412. The top side 404 has a raised portion or bump 414. The plug portion 408 is inserted into the opening of the hose or flexible tubing connected to a suction source. The pull 412 is used to be grasped by a hand to remove the plug portion 408 and the cap device 400 from the hose when a new disposable dental valve device 10, 100, 200, or 300 is to be used. The plug portion 408 may be of a sufficient size and shape to plug an opening associated with a hose attached to a source of suction. The cap device 400 may also be provided separately from the devices 10, 100, 200, and 300. It is also possible that the cap device 400 may be provided as a kit with any of the devices 10, 100, 200, and 300.

The disposable dental valve devices 10, 100, 200, and 300 may be formed of any suitable material such as plastic, polyethylene, and high density polyethylene or any other suitable material that is disposable and recyclable. Any suitable plastic may be used to construct the devices 10, 100, 200, and 300 so that the devices 10, 100, 200, and 300 may withstand use in a dental operation or procedure. It is also possible and contemplated to incorporate an antimicrobial agent or chemical in the plastic or to provide a coating of an antimicrobial agent on the plastic to further prevent cross-contamination when using the devices 10, 100, 200, and 300. As can be appreciated, the antimicrobial agent may be incorporated into any of the components of the devices 10, 100, 200, and 300.

From all that has been said, it will be clear that there has thus been shown and described herein a disposable dental valve device having a check valve which fulfills the various advantages sought therefore. It will become apparent to those skilled in the art, however, that many changes, modifications, variations, and other uses and applications of the subject disposable dental valve device having a check valve are possible and contemplated. All changes, modifications, variations, and other uses and applications which do not depart from the spirit and scope of the disclosure are deemed to be covered by the disclosure, which is limited only by the claims which follow.

What is claimed is:

1. A disposable dental valve device comprises:
   a valve body having a tip receiving end, a hose receiving end, a lumen formed between the tip receiving end and the hose receiving end, a first opening formed in an upper extension portion of the valve body and a second opening formed in a lower extension portion of the valve body; and
   a movable valve sealing device having a bottom side, the movable valve sealing device adapted to being inserted into the first opening and having the bottom side extending out of the second opening, the movable valve sealing device having an opening for alignment with the lumen formed between the tip receiving end and the hose receiving end, the movable valve sealing device having a check valve positioned in the opening, and the movable valve sealing device having a top for positioning the movable valve sealing device between a closed position with the bottom side being within the lower extension portion and an opened position with the bottom side extending out of the second opening of the lower extension portion.

2. The disposable dental valve device of claim 1 wherein the check valve comprises a flap portion.

3. The disposable dental valve device of claim 2 wherein the flap is movable between an opened position and a closed position.

4. The disposable dental valve device of claim 1 wherein the movable valve sealing device and the valve body are each constructed of plastic.

5. The disposable dental valve device of claim 1 wherein an antimicrobial agent is incorporated into the disposable dental valve device.

6. The disposable dental valve device of claim 1 wherein the movable valve sealing device comprises a rectangular panel.

7. The disposable dental valve device of claim 1 wherein the check valve is recessed into the movable valve sealing device.

8. A disposable dental valve device comprises:
   a valve body having a tip receiving end, a hose receiving end, a lumen formed between the tip receiving end and the hose receiving end, an upper extension portion formed in the valve body having an upper opening formed in the upper extension portion and a lower extension portion formed in the valve body having a lower opening formed therein; and a movable valve sealing device having a bottom side, the movable valve sealing device adapted to being inserted into the upper opening and the bottom side extending out of the lower opening in the lower extension portion, the movable valve sealing device having an opening for alignment with the lumen formed between the tip receiving end and the hose receiving end, the movable valve sealing device having a check valve positioned in the opening, and the movable valve sealing device having a top for moving the movable valve sealing device into an opened position with the bottom side extending out of the second opening of the lower extension portion and a closed position with the bottom side being within the lower extension portion.

9. The disposable dental valve device of claim 8 wherein the check valve comprises a flap portion.

10. The disposable dental valve device of claim 9 wherein the flap portion is movable between an opened position and a closed position.

11. The disposable dental valve device of claim 9 wherein the movable valve sealing device further comprises a rectangular panel.

12. The disposable dental valve device of claim 8 wherein the movable valve sealing device and the valve body are each constructed of plastic.

13. The disposable dental valve device of claim 8 wherein an antimicrobial agent is incorporated into the disposable dental valve device.

14. The disposable dental valve device of claim 8 wherein the check valve is recessed into the movable valve sealing device.

15. A disposable dental valve device kit comprising:

a valve body having a tip receiving end, a hose receiving end, a lumen formed between the tip receiving end and the hose receiving end, a first opening formed in an upper extension portion of the valve body and a second opening formed in a lower extension portion of the valve body;

a movable valve sealing device having a bottom side, the movable valve sealing device adapted to being inserted into the first opening and having the bottom side extending out of the second opening, the movable valve sealing device having an opening for alignment with the lumen formed between the tip receiving end and the hose receiving end, the movable valve sealing device having a check valve positioned in the opening, and the movable valve sealing device having a top for positioning the movable valve sealing device between a closed position with the bottom side being within the lower extension portion and an opened position with the bottom side extending out of the second opening of the lower extension portion; and a cap device for insertion into a hose connected to a source of vacuum.

16. The disposable dental valve device kit of claim 15 wherein the cap device comprises a body portion having a plug portion and a pull.

17. The disposable dental valve device kit of claim 15 wherein the cap device is constructed of rubber.

18. The disposable dental valve device kit of claim 15 wherein the cap device is constructed of plastic.

19. The disposable dental valve device kit of claim 15 wherein an antimicrobial agent is incorporated into the cap device.

20. The disposable dental valve device of claim 15 wherein the check valve comprises a flap.

* * * * *